(12) United States Patent
Blurton et al.

(10) Patent No.: US 8,596,280 B2
(45) Date of Patent: *Dec. 3, 2013

(54) APPARATUS AND METHOD OF INHIBITING PERIANAL TISSUE DAMAGE

(75) Inventors: David D. Blurton, Whiteville, TN (US); Hai Trieu, Cordova, TN (US)

(73) Assignee: Plexus Biomedical, Inc., Memphis, TN (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/288,480

(22) Filed: Nov. 3, 2011

(65) Prior Publication Data

US 2012/0053535 A1 Mar. 1, 2012

Related U.S. Application Data

(63) Continuation of application No. 12/720,347, filed on Mar. 9, 2010, now Pat. No. 8,066,009, which is a continuation of application No. 11/743,858, filed on May 3, 2007, now Pat. No. 7,673,633.

(60) Provisional application No. 60/746,283, filed on May 3, 2006.

(51) Int. Cl.
*A61B 19/00* (2006.01)
*A61F 2/00* (2006.01)
*A61F 2/02* (2006.01)
*A61F 5/44* (2006.01)

(52) U.S. Cl.
USPC .............................. 128/887; 600/32; 604/338

(58) Field of Classification Search
USPC ................... 600/29–32, 38–39; 604/329–332, 604/337–338; 482/10, 11, 27, 127; 128/DIG. 25, 845
See application file for complete search history.

(56) References Cited

U.S. PATENT DOCUMENTS

| 1,511 A | 3/1840 | Truss |
|---|---|---|
| 316,903 A | 4/1885 | Lytle |
| 453,880 A | 6/1891 | Coffee |
| 942,590 A | 12/1909 | Sanborn |
| 969,134 A | 8/1910 | Cowie |
| 1,249,195 A | 12/1917 | Raines |
| 1,547,127 A | 7/1925 | Metzger |
| 1,711,294 A | 4/1929 | Weitzner |

(Continued)

FOREIGN PATENT DOCUMENTS

| GB | 1127548 A | 9/1968 |
|---|---|---|
| JP | 7-275309 | 10/1995 |

(Continued)

OTHER PUBLICATIONS

Abramowitz et al., "Epidemiology of anal lesions (fissure and thrombosed external hemorroid) during pregnancy and post-partum", Gynecol Obstet Fertil 2003, No. 31, 546-549.

(Continued)

*Primary Examiner* — Patricia Bianco
*Assistant Examiner* — Tarla Patel
(74) *Attorney, Agent, or Firm* — Haynes and Boone, LLP

(57) ABSTRACT

A perianal support device is provided that is configured to inhibit the formation and/or progression of tissue damage in the perianal region of the body. A method is provided to apply the perianal support device to patients during childbirth to inhibit the formation and/or progression of tissue damage in the perianal region of the body.

10 Claims, 12 Drawing Sheets

(56) References Cited

U.S. PATENT DOCUMENTS

| | | |
|---|---|---|
| 1,877,766 A | 9/1932 | Kennedy |
| 2,128,670 A | 8/1938 | Bolder |
| 2,468,348 A | 4/1949 | Shore |
| 2,653,599 A | 9/1953 | Bell |
| 3,712,300 A | 1/1973 | Davidowitz |
| 3,826,242 A | 7/1974 | Eggers |
| 3,939,842 A | 2/1976 | Harris |
| 4,240,436 A | 12/1980 | Singleton |
| 4,263,914 A | 4/1981 | Pawlak |
| 4,365,631 A | 12/1982 | Kline |
| 4,421,504 A | 12/1983 | Kline |
| 4,439,180 A | 3/1984 | Kline |
| 4,445,899 A | 5/1984 | Bond |
| 4,484,919 A | 11/1984 | Sohn et al. |
| 4,583,542 A | 4/1986 | Boyd |
| 4,638,806 A | 1/1987 | Bartlett |
| 4,670,419 A | 6/1987 | Uda et al. |
| 4,891,847 A | 1/1990 | Baker et al. |
| 5,178,627 A | 1/1993 | Hudock |
| 5,263,926 A | 11/1993 | Wilk |
| 5,676,637 A | 10/1997 | Lee |
| 5,695,484 A | 12/1997 | Cox |
| 5,704,894 A | 1/1998 | Boutos |
| 5,800,485 A | 9/1998 | Trop et al. |
| 5,908,379 A | 6/1999 | Schaefer et al. |
| 5,924,423 A | 7/1999 | Majlessi |
| 5,935,595 A | 8/1999 | Steen |
| 6,083,241 A | 7/2000 | Longo et al. |
| 6,102,271 A | 8/2000 | Longo et al. |
| 6,142,933 A | 11/2000 | Longo et al. |
| D437,642 S | 2/2001 | Caballero |
| 6,364,852 B1 | 4/2002 | Lee |
| 6,428,004 B1 | 8/2002 | McQuitty et al. |
| 6,503,192 B1 | 1/2003 | Ouchi |
| 6,517,562 B1 | 2/2003 | Holland |
| 6,537,132 B1 | 3/2003 | Alberts |
| 6,627,632 B2 | 9/2003 | Parks et al. |
| 6,712,841 B2 | 3/2004 | Gomez |
| 6,716,229 B2 | 4/2004 | Toth |
| 6,913,573 B1 | 7/2005 | Viscomi et al. |
| 6,916,494 B2 | 7/2005 | Park |
| 6,991,813 B2 | 1/2006 | Xu |
| 7,160,294 B2 | 1/2007 | Croft |
| 7,673,633 B2 | 3/2010 | Blurton et al. |
| 7,766,931 B2 | 8/2010 | Blurton |
| 8,062,277 B2 | 11/2011 | Fleming |
| 8,277,427 B2 | 10/2012 | Edvardsen et al. |
| 8,353,884 B2 | 1/2013 | Hansen et al. |
| 2001/0000731 A1 | 5/2001 | Jia et al. |
| 2001/0003157 A1 | 6/2001 | Toth |
| 2002/0072522 A1 | 6/2002 | Parks et al. |
| 2002/0142902 A1 | 10/2002 | Stein |
| 2002/0147482 A1 | 10/2002 | Carter |
| 2002/0187990 A1 | 12/2002 | Parks et al. |
| 2002/0192273 A1 | 12/2002 | Buseman et al. |
| 2003/0021850 A1 | 1/2003 | Xu |
| 2003/0229263 A1 | 12/2003 | Connors et al. |
| 2003/0236442 A1 | 12/2003 | Connors et al. |
| 2004/0076688 A1 | 4/2004 | Park |
| 2004/0088031 A1 | 5/2004 | Gomez |
| 2004/0217146 A1 | 11/2004 | Beck |
| 2004/0254590 A1 | 12/2004 | Hoffman et al. |
| 2005/0000003 A1 | 1/2005 | Bushelman |
| 2005/0049660 A1 | 3/2005 | Croft |
| 2005/0214327 A1 | 9/2005 | Brooks et al. |
| 2006/0025766 A1 | 2/2006 | Heinrich et al. |
| 2006/0144897 A1 | 7/2006 | Jankowski et al. |
| 2006/0153927 A1 | 7/2006 | Xu |
| 2006/0155340 A1 | 7/2006 | Schuler et al. |
| 2006/0195146 A1 | 8/2006 | Tracey et al. |
| 2006/0195153 A1 | 8/2006 | DiUbaldi et al. |
| 2006/0198883 A1 | 9/2006 | Parks et al. |
| 2007/0011802 A1 | 1/2007 | Holland |

FOREIGN PATENT DOCUMENTS

| | | |
|---|---|---|
| JP | 2001-129004 | 5/2001 |
| JP | 2001170093 | 6/2001 |
| WO | WO02/13680 A2 | 2/2002 |
| WO | WO03/053255 A1 | 7/2003 |

OTHER PUBLICATIONS

Danel, "Magnitude of Maternal Morbidity During Labor and Delivery: United States, 1993-1997", American Journal of Public Health, Apr. 2003, vol. 93, No. 4 pp. 631-634.

International Search Report and Written Opinion of the International Searching Authority for PCT/US06/29583 dated Aug. 3, 2007, 9 pages.

Masahiro Takana, Anal Diseases, Pregnancy and Parturition, 1990, Nippon Daicho Komonbyo Gakkai Zasshi, Takyo, 1990; 43(6); pp. 1077-82; with English translation, 64 pages.

U.S. Appl. No. 11/197,627, filed Aug. 5, 2005; Final Office Action mailed Sep. 10, 2009, 17 pages.

U.S. Appl. No. 11/197,627, filed Aug. 5, 2005; Interview Summary mailed Nov. 3, 2009, 6 pages.

U.S. Appl. No. 11/197,627, filed Aug. 5, 2005; Amendment (with Affidavit) filed Nov. 10, 2009, in response to Final Office Action, 32 pages.

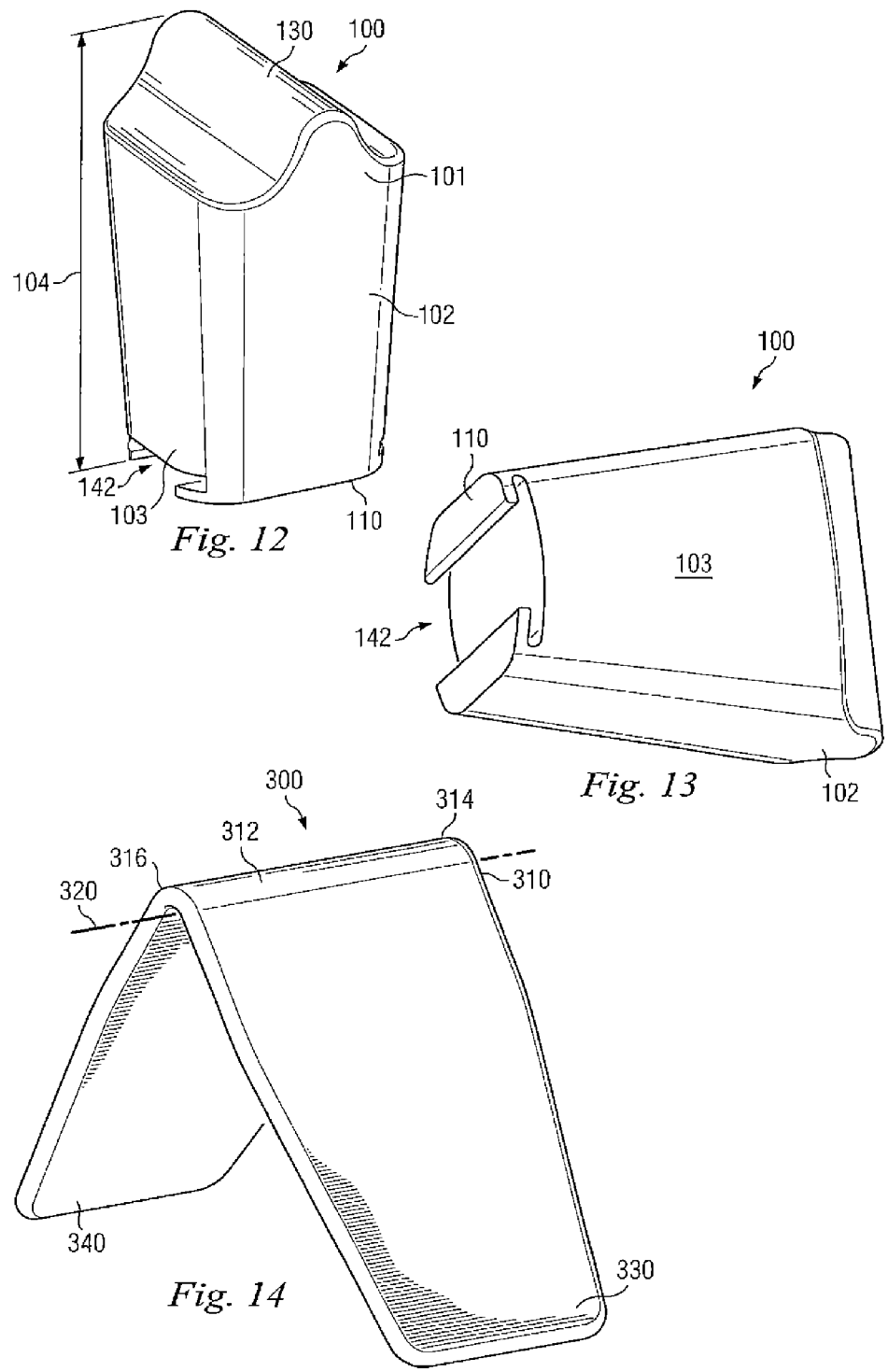

APPARATUS AND METHOD OF INHIBITING PERIANAL TISSUE DAMAGE

CROSS REFERENCE TO RELATED APPLICATIONS

This application is a continuation of U.S. Ser. No. 12/720,347 filed on Mar. 9, 2010, which is a continuation of U.S. Ser. No. 11/743,858 filed on May 3, 2007, which claims the benefit of U.S. Provisional Application No. 60/746,283 filed on May 3, 2006 and incorporated by reference herein. The present application claims the benefit of each of the foregoing applications. In addition, U.S. patent application Ser. No. 11/197,627 filed Aug. 5, 2005 entitled Method, Apparatus and System for Preventing or Reducing the Severity of Hemorrhoids commonly assigned to the present applicant is hereby incorporated by reference in its entirety.

BACKGROUND

The disclosed embodiments relate to a method and apparatus for inhibiting perianal tissue damage. The child birthing process is a traumatic event for a women's body and can result in tissue damage; such as fissures, tears and bulging, in and around the anus as a result of pushing the baby into and/or through the birthing canal. Even when labor does not result in a vaginal delivery, the process of pushing during labor may also result in the development of or increase in severity of hemorrhoids. Current birthing techniques do not provide an apparatus or method for supporting the soft perianal tissues near the anal orifice.

Thus, there is a need for devices and methods that provide support to the perianal tissues. In some aspects, these devices and methods may be useful in preventing or reducing the severity of hemorrhoids and other tissue damage, during the child birthing process.

SUMMARY

In one embodiment, a system for perianal tissue support is provided. The support includes a support body having a midline perianal tissue pressure member with a lateral anchoring assembly joined to the support body and extending away from the support body in a direction substantially transverse to the midline of the pressure member. In a further aspect, the anchoring assembly includes a mechanism for applying force to the support body to compressively load the pressure member against the perianal tissue of the patient.

In another embodiment, a support device for use on a patient is provided. The support device comprises a body configured for at least partial placement in the cleft of the buttocks, the cleft having a depth measured in the sagittal plane of the patient. The body includes a contact surface configured to support a perianal region and a compression member extending from the body. The compression member has a length in the saggital plane that is greater than the depth of the gluteal cleft.

In still a further embodiment, a method is provided. The method includes providing a support member having a pressure surface configured for engaging the perianal area of a patient and an elongated compression member. The method includes positioning the pressure surface proximate the perianal area of a patient with the compression member extending outwardly beyond the crown of the buttocks, and applying pressure to the compression member to direct pressure through the pressure surface against the perianal area of the patient. In one aspect, the method includes securing at least the compression member to inhibit movement. In still a further aspect, the securing includes adhering a portion of an elongated member to the patient.

In yet another embodiment, there is provided a kit for applying to the perianal region of a patient. In one aspect, the kit includes a perianal support member and an anchoring system. In a further aspect, the anchoring system includes a mechanism for applying force to the perianal support member to compressively load the perianal tissue of the patient. In a further aspect, the kit includes a treating compound.

In one embodiment, a perianal support device for a patient is provided. The device comprises a perianal support body having a pressure surface configured to engage perianal tissue and a system for applying pressure. The pressure applying system has a first portion engagable to the support body and a second portion extending away from the support body. The pressure applying system is configured to force the pressure surface to press against the perianal tissue.

In a further embodiment, a method is provided for fixing a perianal support device to a patient to compressively load the perianal tissue.

Further aspects, forms, embodiments, objects, features, benefits, and advantages of the present disclosure shall become apparent from the detailed drawings and descriptions provided herein.

BRIEF DESCRIPTION OF THE DRAWINGS

FIG. 12 is a first perspective view of a still a further embodiment according to another aspect of the present invention;

FIG. 13 is a second perspective view, of the embodiment of FIG. 12;

FIG. 14 is a perspective view of another embodiment according to a further aspect of the present invention;

DETAILED DESCRIPTION

Figure 1:
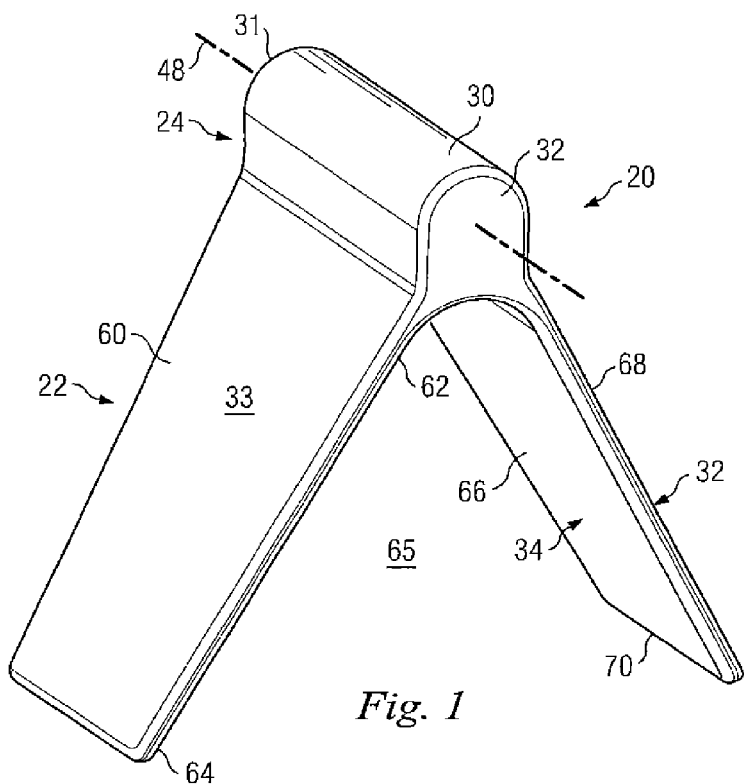
FIG. 1 is a perspective view of one aspect of an apparatus according to a first embodiment.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 2:
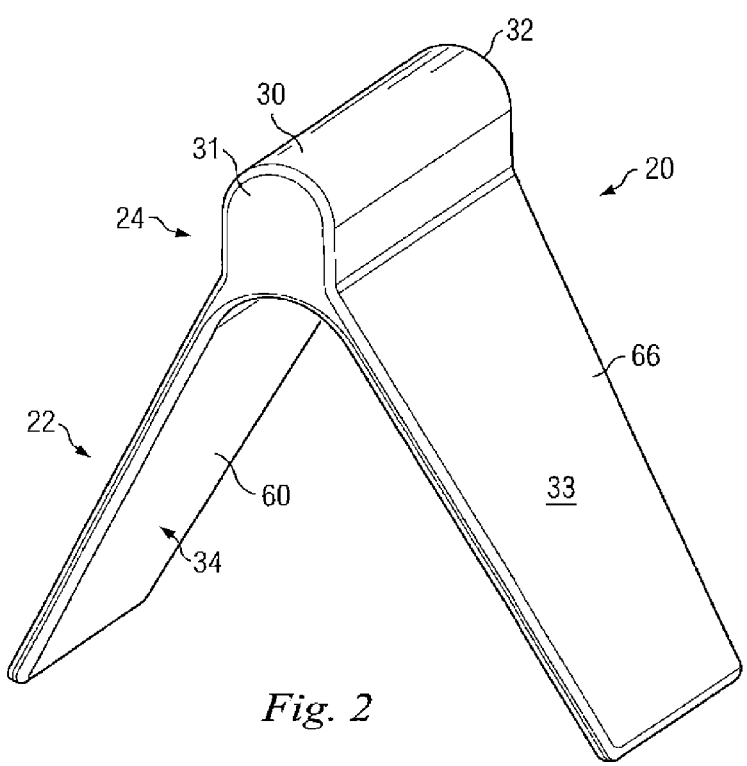
FIG. 2 is a perspective view, opposite to the view of FIG. 1, of the apparatus of FIG. 1.
Figure 3:
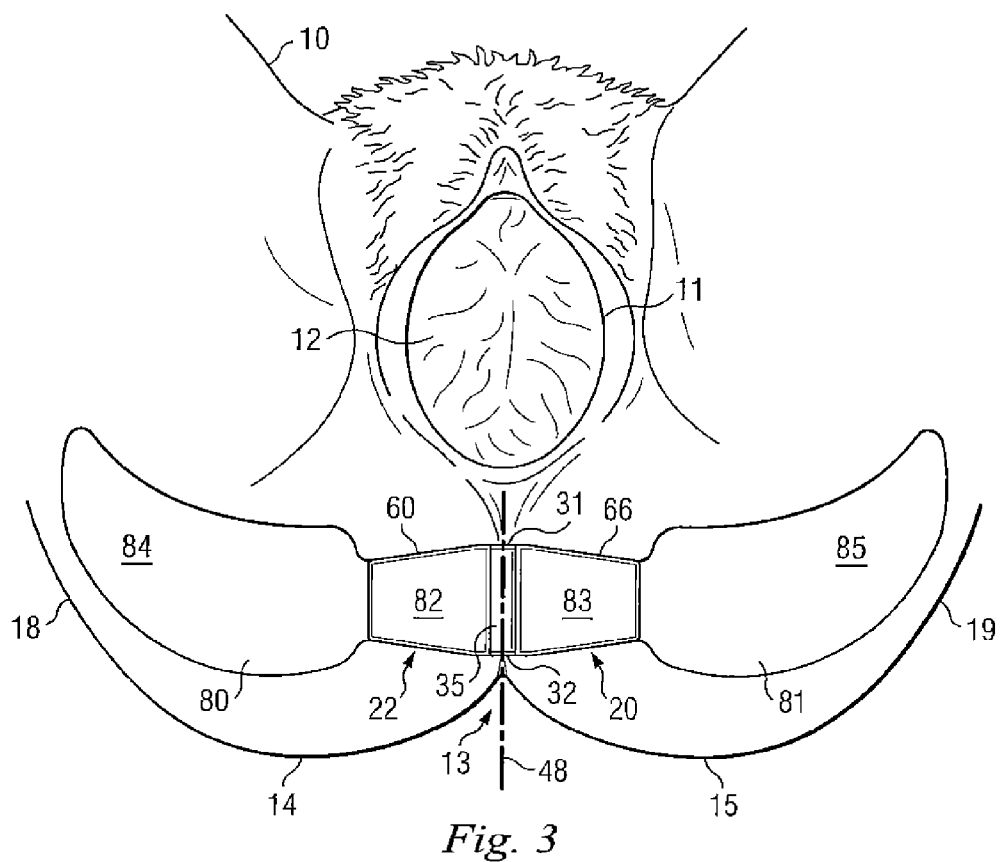
FIG. 3 is a partial perspective bottom view of the apparatus of FIG. 1 affixed to a patient during child delivery.
Figure 4:
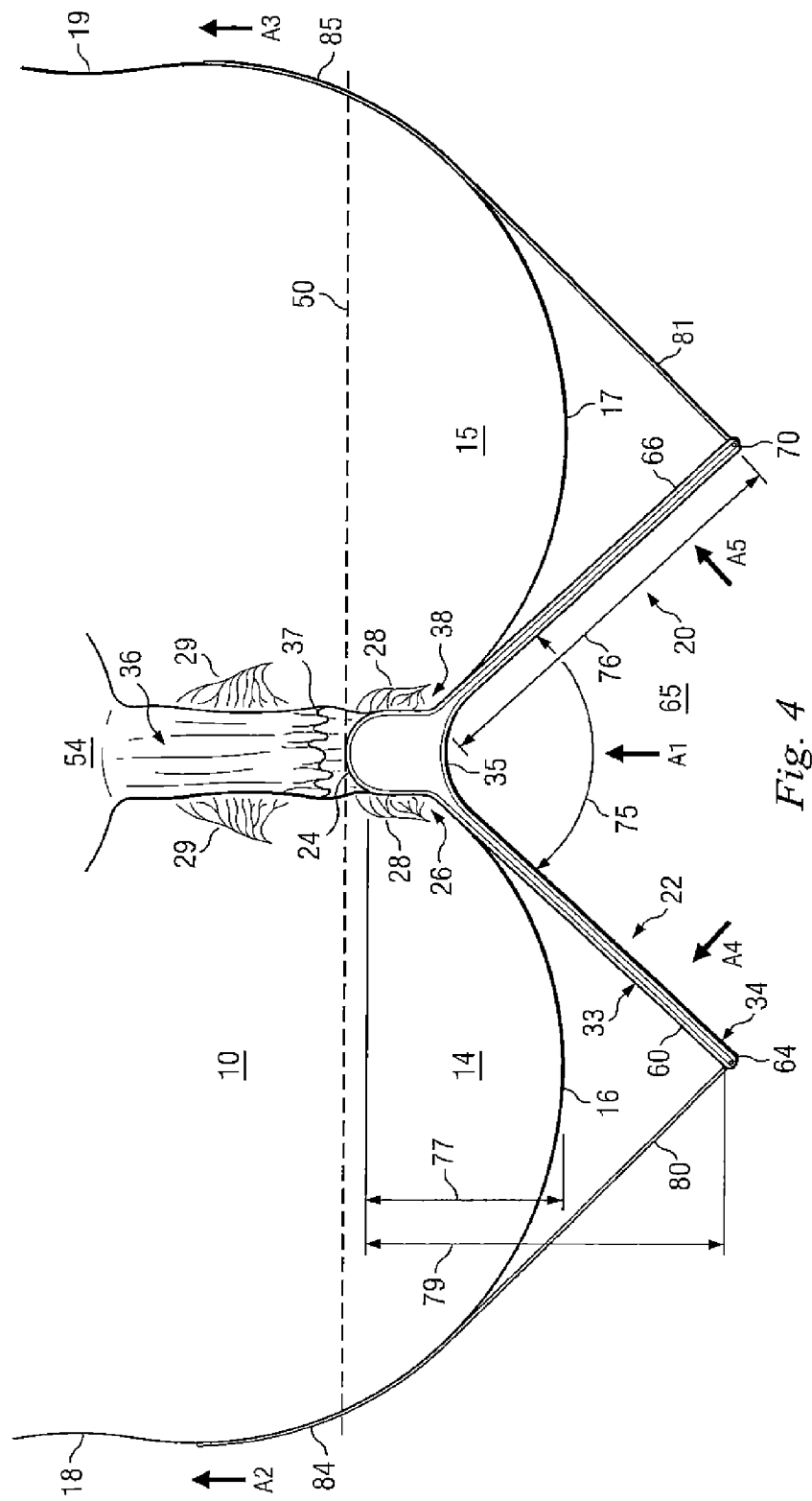
FIG. 4 is a partial cross sectional top view of FIG. 3, showing stylized patient anatomy and the applied apparatus.
Figure 5:
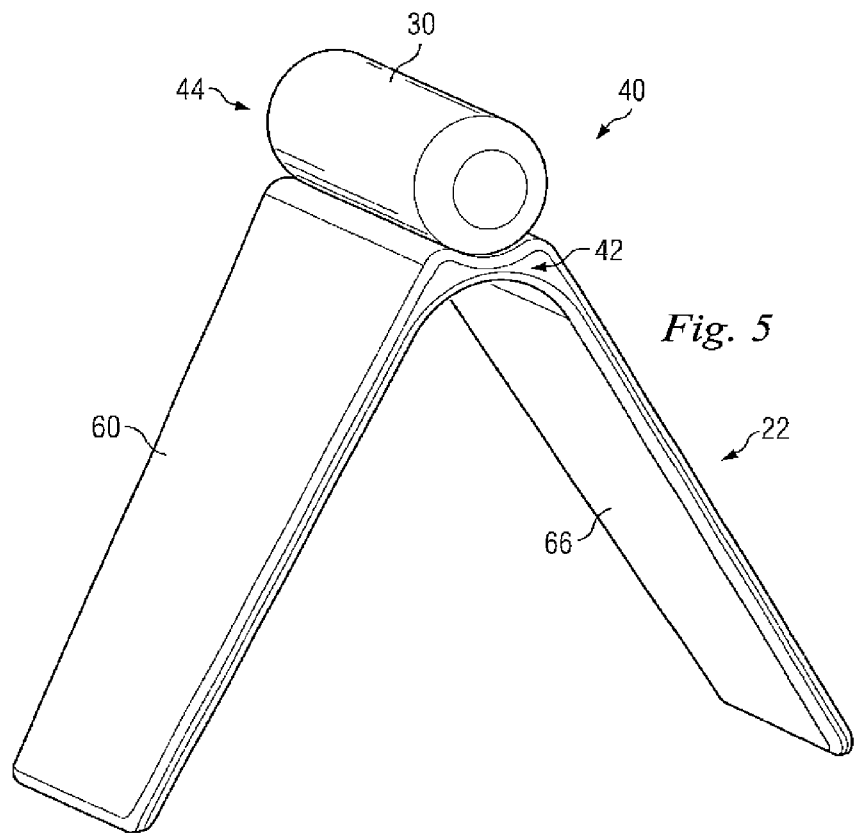
FIG. 5 is a perspective view of another embodiment of the present invention.
Figure 6:
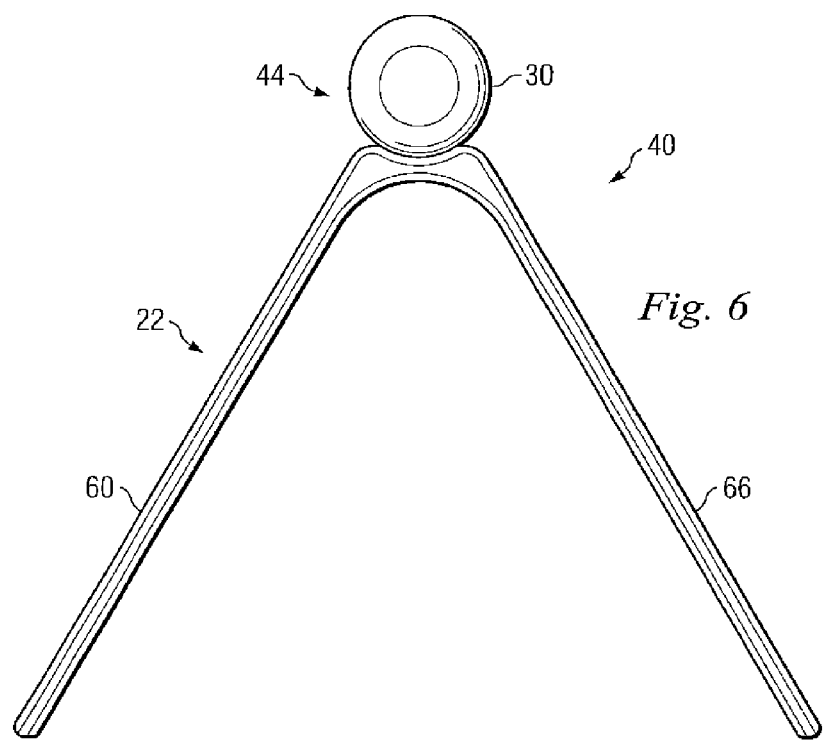
FIG. 6 is an end view of the apparatus of FIG. 5.
Figure 7:
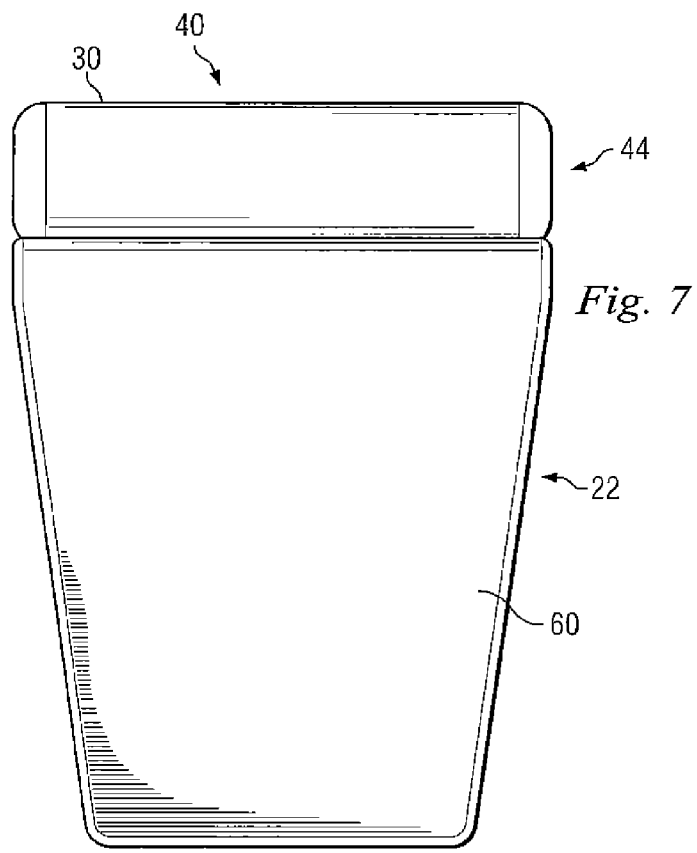
FIG. 7 is a side view of the apparatus of FIG. 5.
Figure 8:
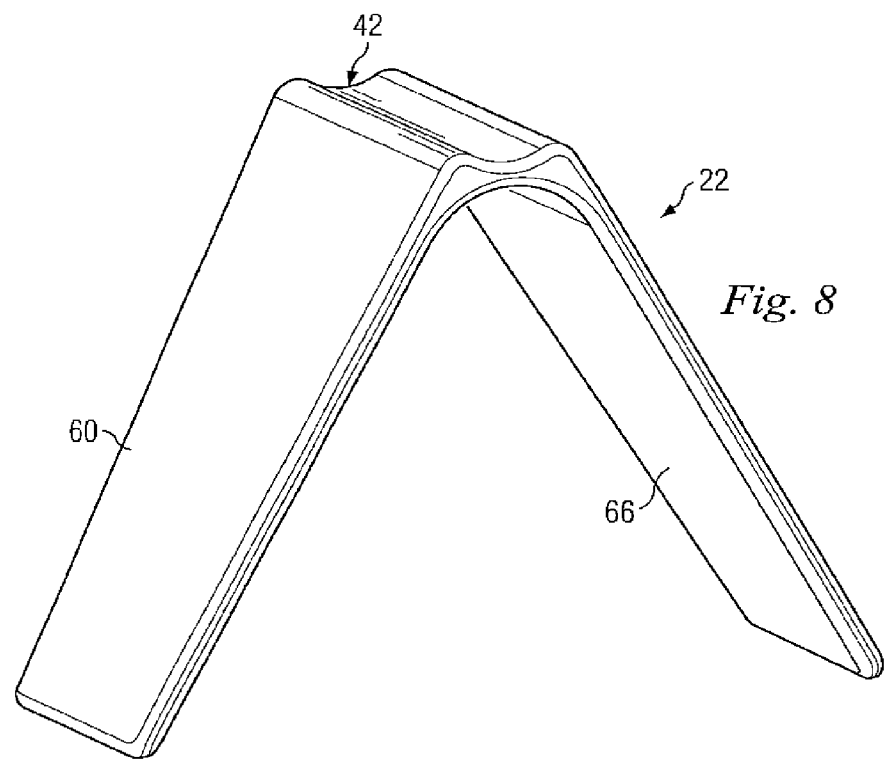
FIG. 8 is a perspective view of one aspect of the base of the apparatus of FIG. 5.

Referring now to FIGS. 1-4, a support system according to one embodiment of the present invention is illustrated in association with the perianal tissue of a patient 10. In FIG. 4, the patient 10 is shown in partial cross section to illustrate a portion of the rectum 54, anal canal 36, anal orifice 38, internal venous plexus 29, pectinate line 37 (also known as the dentate line), and external venous plexus 28. The patient's buttocks 14 and 15 are shown with the crown of the buttocks 16 and 17, respectively, laterally adjacent the perianal region 26. The gluteal cleft 13 (FIG. 3) is between buttocks 14 and 15. The buttocks 14 and 15 extend laterally beyond crowns 16 and 17 toward lateral flanks 18 and 19, respectively. The crowns 16 and 17 of each buttocks 14 and 15 in essence define the midline of each leg and the lateral flanks 18 and 19 are the area lateral of the leg/buttocks midline. The lateral flanks 18 and 19 may include, for example but without limitation, all or a portion of the lateral buttocks, hips, or upper thigh of the patient.

During the child birthing process, contractions during labor move a child 12 into the birth canal and ultimately, for a vaginal delivery, through the vaginal opening 11, as shown in FIG. 3. In an alternative birthing process, labor is commenced to move the child 12, but for a variety of reasons, the delivery does not occur vaginally but instead caesarian delivery is performed through a surgical opening in the mother's abdomen. During the birthing process, tremendous pressure is exerted in an effort to move the child toward delivery. At least some of this pressure is exerted against the tissues adjacent the anal orifice 38 in the perianal region 26. The result of these forces is that blood vessels near the anus, such as those in the external venous plexus 28, may bulge or rupture causing hemorrhoids or increasing their severity. Still further, other tissues in the perianal region 26 adjacent the anus may distend outwardly opposite arrow A1 in FIG. 4 causing lacerations such as tearing around the vaginal opening or fissures from the anus. In addition to the blood loss, pain, and discomfort, these lacerations can be a location for infections in the mother. The present invention provides devices to support the perianal tissues during the birthing process without interfering with the birthing canal or vaginal opening 11 and/or allowing easy removal to access the perianal region 26. Still further, methods are provided to support the perianal tissue to inhibit damage to the tissue near the anal orifice 38, both internally and externally, to inhibit, for example but without limitation to other actions, the formation or advancement of external hemorrhoids and/or to inhibit the formation or advancement of lacerations of the perianal tissues.

Referring to FIGS. 1 and 2, there is shown an embodiment of one aspect of a tissue support device 20 according to the present invention. Support device 20 includes a base 22 having a raised portion 24 extending generally along contact axis 48. In the illustrated embodiment, the raised portion 24 defines a partial cylinder having a curved pressure surface 30 oriented to extend along contact axis 48 between the posterior end 31 and the anterior end 32. A first flange 60 has a first end portion 62 joined to the raised portion 24 and an opposing second end portion 64. An opposing second flange 66 has a first end portion 68 joined to the raised portion 24 and an opposing second end portion 70. The device 20 includes an outer surface 33 and an opposing inner surface 34 defining an access cavity 65. As shown in FIGS. 3 and 4, a securing member 80 is attached to first flange 60 adjacent end portion 64. In a similar manner, a second securing member 81 is attached to second flange 66 adjacent end portion 70. In the illustrated embodiment, securing members 80 and 81 are elongated, flexible strips of adhesive tape. Midline end portions 82 and 83 of the securing members 80 and 81 are adhered to the inner surface 34 of the support device 20 while the opposing lateral ends 84 and 85 extend outwardly laterally from the midline or contact axis 48 of the device.

Referring to FIG. 4, in use, a health care provider positions the patient 10 to expose the perianal region 26. In the child birthing process, the patient 10 may be positioned in stirrups attached to a delivery table (not shown). The perianal support device 20 is then moved adjacent the gluteal cleft 13 between buttocks 14 and 15. The support device 20, is positioned such that the midline 48 of the support device is substantially aligned with the patient's midline within the sagittal plane. Referring to FIG. 4, the support device 30 is advanced in the direction of arrow A1 toward the anal orifice 38 (generally within the sagittal plane toward the head of the patient) to bring pressure surface 30 into contact with the perianal tissues. Continued advancement of the support device 20 toward the anal orifice 38 applies pressure through the pressure surface 30 to the perianal tissues. In one aspect, the healthcare provider places at least one finger within the access cavity 65 and preferably against internal contact surface 35 to advance the device against the anal orifice 38. With continued pressure applied by the healthcare provider to the access cavity 65, and/or internal contact surface 35, fixation member 80 is extended laterally of the anal orifice 38 out of the gluteal cleft 13 and releasably attached to the patient 10 to at least the lateral flank 18. In a similar manner, with compressive force applied by the healthcare provider to support device 20, elongate fixation member 81 is extended laterally of the anal orifice 38 out of the gluteal cleft 13 and is secured to the patient adjacent lateral flank 19. Thus, the fixation members 80 and 81 of the system do not extend along the patient midline in the gluteal cleft 13 with the potential for interference with the birthing process, but instead extend substantially laterally from the patient's midline out of the gluteal cleft 13 and are attached at the patient's lateral flanks 18 and 19.

The extent of tissue deformation surrounding the anal orifice 38 when device 20 is applied is a function of the patient anatomy and of the amount of compressive force applied during application of the support device 20. As shown in FIG. 4, the maximum extent of perianal tissue engagement inwardly on the patient in the saggital plane is shown by line 50. In one aspect, it is contemplated that pressure applied in the direction of arrow A1 moves the anal orifice inwardly 1 cm to 3 cm. In one embodiment, the lateral ends 84 and 85 of the fixation members 80 and 81 extend beyond line 50 generally in the patient's saggital plane. The fixation members 80 and 81 exert tension forces generally in the direction of arrows A2 and A3, respectively. This tension force is applied to flanges 60 and 66, which are substantially rigid members capable of transmitting compressive forces to the raised body 24. The tension force applied on the lateral flanks 18 and 19 of the patient 10 in the direction of arrows A2 and A3 is converted to compressive forces in the direction of arrows A4 and A5, respectively. The compressive forces A4 and A5 are transmitted by substantially rigid flanges 60 and 66 to raised body 24 and ultimately to compression surface 30 to apply support and/or pressure to the perianal tissues in the direction of arrow A1. It will be appreciated that the lateral components of compressive forces applied in A4 and A5 helps to maintain the position of device 20 as well as tending to maintain access cavity 65 in an open position.

As shown in FIG. 4, flanges 60 and 66 each extend for a length 76 from the internal contact surface 35 to their proximal ends 64 and 70, respectively. In one aspect, length 76 is greater than 5 cm but less than 20 cm. In the illustrated embodiment, length 76 is approximately 8 cm. The flanges 60 and 66 extend away from each other to define access cavity 65 by an internal angle 75. In one aspect, the angle 75 is between 30 and 140 degrees. In the illustrated embodiment, angle 75 is approximately 90 degrees. The distance 77 between the anal orifice and the buttocks crown 16 is less than the distance 79 between the distal end 64 of the flange 60 and the anal orifice. Thus, tension applied to fixation members 80 and 81 is transferred through substantially rigid flange 60 to exert a compressive force on pressure surface 30 in the direction of arrow A1. Whereas, if distance 77 is greater than distance 79 tension applied to fixation members 80 and 81 may pull the device 20 in a direction opposite arrow A1.

It will be appreciated that with the illustrated embodiment, the healthcare provider may reposition the device 20 and adjust the compressive force applied through the fixation members 80 and 81 to the pressure surface 30 by releasing or adjusting the attachment between the fixation members 80 and 81 and the patient 10.

Referring now to FIGS. 5-8, there is shown a further embodiment of a tissue supporting apparatus according to the present invention. Similar references numerals will be used to refer to components similar to the previously described embodiment. Device 40 comprises a base 22 having an extending raised portion 44 that, when positioned against a patient 10 (see FIGS. 3 and 4), applies pressure to a perianal region 26 adjacent to an external rectal venous plexus 28 to support the perianal tissue to prevent and/or reduce the severity of hemorrhoids and other tissue damage. The device may be secured to the patient as described above. Base 22 may be integrally formed with the raised portion, such as raised portion 24 shown in FIG. 1, or alternatively base 22 and the raised portion 44 may be removably connected, such as shown in FIGS. 5-8. For example, device 40 further includes a securing mechanism 42 operable to fix base 22 to the raised portion 44. For example, securing mechanism 42 may include, but is not limited to, one or any combination of an interlocking mechanical interface, such as a dovetail, a separate mechanical connector, or a chemically-based fixator, such as a glue.

Figure 9:
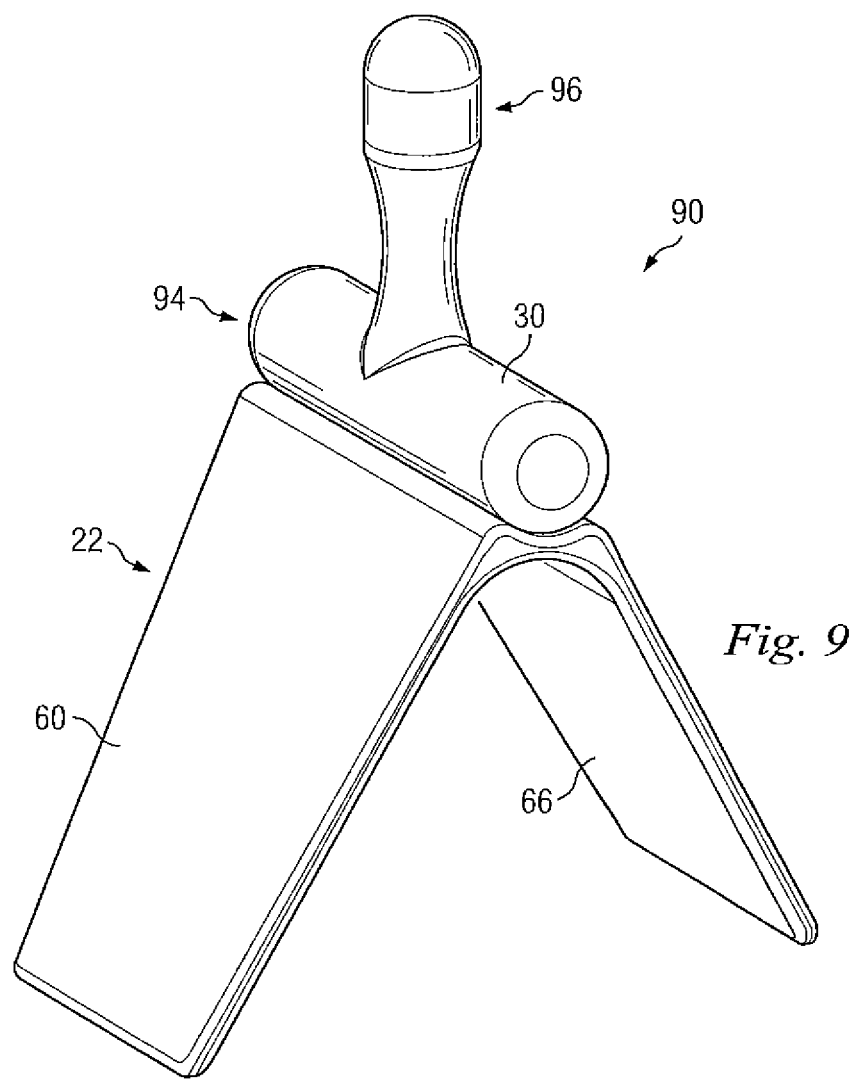
FIG. 9 is a perspective view of a further embodiment of the present invention.
Figure 11:
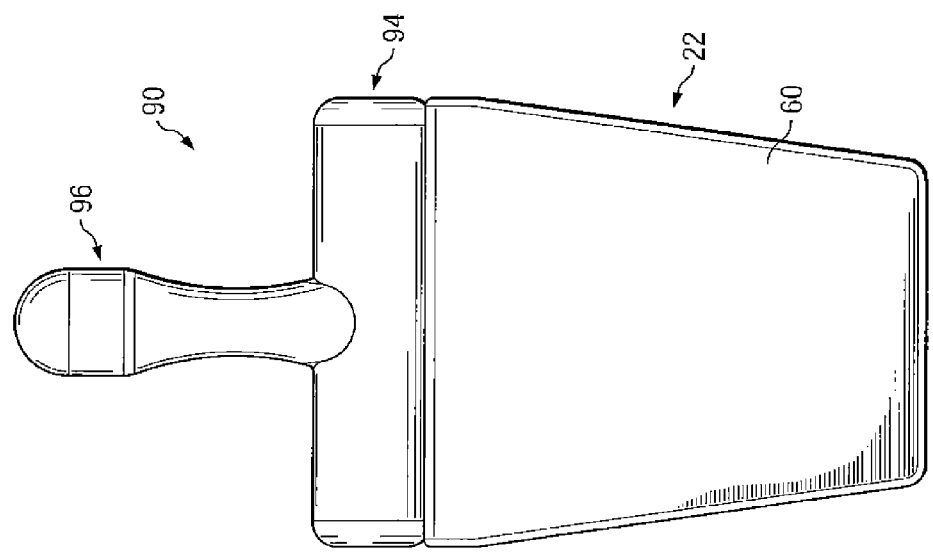
FIG. 11 is a side view of the apparatus of FIG. 9.
Figure 10:
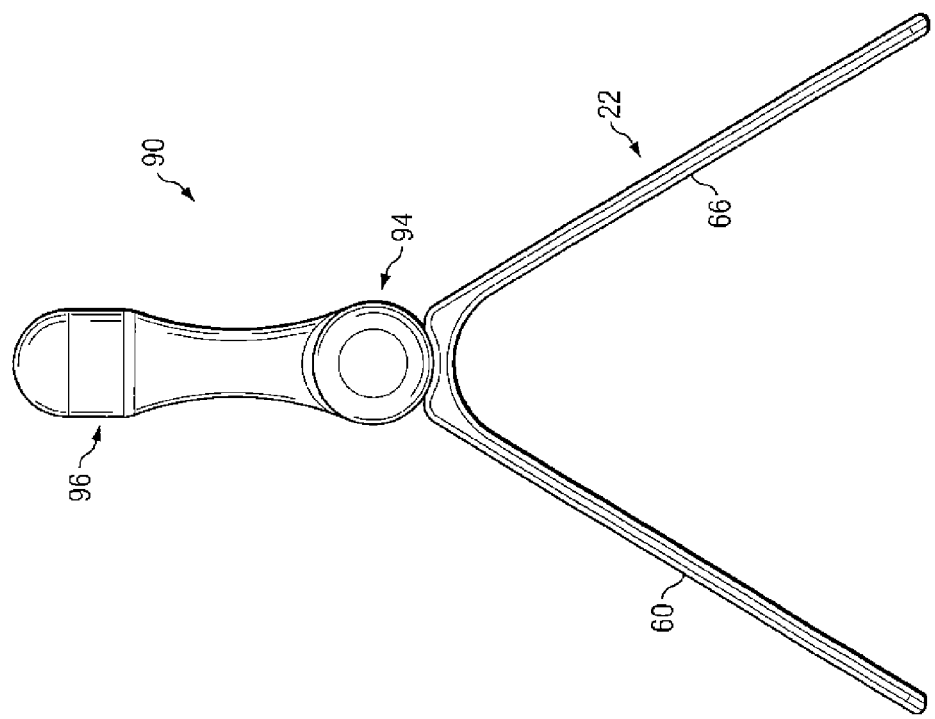
FIG. 10 is an end view of the apparatus of FIG. 9.

In still a further embodiment illustrated in FIGS. 9-11, the device 90 includes a raised portion 94 attached to base 22 having outwardly extending legs 60 and 66 defining a V-shaped body. Extending from the pressure surface 30 is a plug portion 96 may be shaped and sized for insertion within anal canal 36 of patient 25. All or a portion of plug 96 may provide pressure to oppose the distension of vascular tissue, such as internal rectal venous plexus 29 and external rectal venous plexus 28, shown in FIG. 4, by placement within anal canal 36 and/or adjacent rectum 54. As such, plug portion 96 may apply pressure to prevent or reduce the severity of thrombosed internal hemorrhoids. Plug portion 96 has an enlarged distal end to resist expulsion from anal canal 36. It will be appreciated that pressure surface 30 may be substantially rigid in comparison to the adjacent soft tissue while plug portion 96 may be formed a significantly more pliable material that is deformable as the child 12 passes through the birth canal and out of the vaginal opening 11. The flanges 60 and 66 are configured to engage the skin of the patient laterally adjacent the anal orifice and assist in maintaining the position thereof. It will be appreciated that in addition to the enlarged plug 96 and flanges 60 and 66, fixation members 80 and 81 may also be used to maintain the position of the device on the patient and supply compressive force to compression surface 30.

Referring now to FIGS. 12 and 13, support device 100 is shown as a further embodiment of the present invention. Support device 100 includes a base member 101 with a raised compression surface 130 configured for engagement with the anal orifice 38 and surrounding tissue. The substantially solid base 101 has a first lateral side wall 103 and an opposing lateral side wall extending substantially parallel to each other and parallel to the midline of the compression surface 130. The base has a base extension 102 that extends from the compression surface 130 to the proximal end 110 a distance 104. In a preferred aspect, the distance 104 is greater than the depth of the patient's gluteal cleft 13 such that it extends outward beyond the perimeter of the patient. The proximal end 110 includes a channel 142. A strap or other fixation member (not shown), such as members 80 and 81, is passed through channel 142. The fixation member is then secured to the patient 10 or to a stationary object to secure the device 100 in position and allow the base extension 102 to be utilized to aid in transferring force from base 101 to compression surface 130. In one aspect, the base 101 is a substantially solid, rigid member formed from a unitary material. In another aspect, the compression surface 130 is formed of a more compliant material than the material forming base 101.

Additionally, flanges 60 and 66 may be positioned so as to extend away from base portion 72 and/or a respective raised portions 24, 44 and 94. Further, flanges 60 and 66 may be respectively positioned at a predetermined angle 75 such that flanges 60 and 66 diverge as they extend away from respective raised portion 24, 44 and 94. For example, in some aspects, predetermined angle 75 may be in the range of about 50 degrees to about 120 degrees, while in other aspects predetermined angle 75 may be in the range of about 70 degrees to about 90 degrees, while in other aspects predetermined angle 75 may comprise any angle operable to position flanges 60 and 66 against the local anatomy of patient 10 while positioning the respective raised portion 24, 44 and 94 in perianal region 26 to apply pressure to prevent or reduce the severity of hemorrhoids.

Additionally, in the illustrated embodiments, each device 20, 40, 90, and 100 are sized and positioned with respect to patient 10 to allow for the passage of a child through the birthing canal during childbirth. It is contemplated that the devices may be placed to support more or less of the perineum between the anus and vaginal opening depending on the health care provider's judgment and the progress of the child birthing process. Still further, it is contemplated that an elongated anterior to posterior device may be positioned to support at least a portion of the perianal tissue and the vaginal tissue during the labor process. It is anticipated that the supporting device will be repositioned posteriorly away from the vaginal opening prior to delivery of the child through the vaginal opening.

Devices 20, 40, 90, and 100 may be formed of a raised portion that generally conforms to the patient's anatomy, while the base is substantially rigid so as to resist deformation and transfer compressive force from fixation mechanism to raised portion. For example, the raised portion may be formed from one or any combination of silicone or any type of elastomeric material, while base may be formed from a plastic, vinyl, polyvinylchororide, acrylic, and/or polycarbonate material. In other aspects, the entire device 20, 40, 90, and 100 may be substantially rigid.

Figure 15:
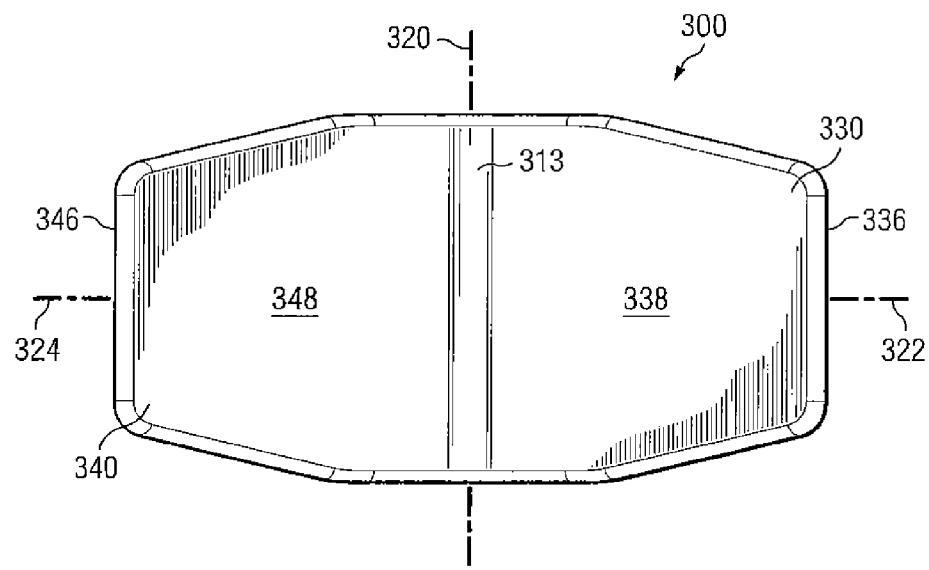
FIG. 15 is a top view of the embodiment of FIG. 14.
Figure 16:
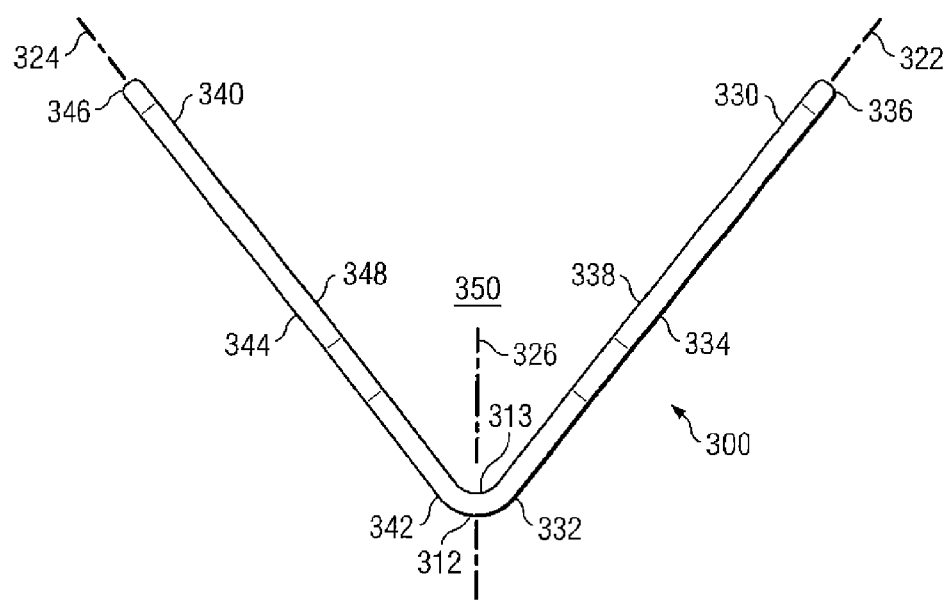
FIG. 16 is an end view of the embodiment of FIG. 14.

Referring now to FIGS. 14-16, there is shown another embodiment of a perianal support device 300 according to the present invention. Support device 300 includes a base 310 having an external pressure surface 312. The external pressure surface 312 extends along midline axis 320 between first end 314 and opposing second end 316. A pair of opposing compression members 330 and 340 is joined to base 310. In the illustrated embodiment, compression members 330 and 340 are integral with and define a portion of base 310. The compression member 330 includes a distal end 332 transitioning into pressure surface 312, an elongated, planar exterior side wall 334 extending from distal end 332 to proximal end 336. The compression member 330 extends generally along axis 322 which is substantially transverse to midline axis 320 as shown in the top view of FIG. 15. In the end view of FIG. 16, it is shown that compression member 330 extends at an oblique angle with respect to axis 326. It will be understood that axis 326 is also representative of the sagital plane of the body and midline axis 320 extends generally within the sagittal plane. In a similar manner, the compression member 340 includes a distal end 342 transitioning into pressure surface 312, an elongated, planar exterior side wall 344 extending from distal end 342 to proximal end 346. The compression member 340 extends generally along axis 324 which is substantially transverse to midline axis 320 as shown in the top view of FIG. 15. In the end view of FIG. 16, it is shown that compression member 340 extends at an oblique angle with respect to axis 326. It will be appreciated that in the illustrated embodiment, compression member 330 extends at an oblique angle substantially equal to the oblique angle at which compression member 340 extends with respect to axis 326.

The perianal support device 300 has an internal contact surface 313 defined along the midline 320 opposing the exterior pressure surface 312. It will be understood that a health care provider may apply pressure to the contact surface 313 to move the support device 300 into the operative position and/ or apply additional pressure to compress at least some perianal tissues. The compression member 330 includes an interior wall 338 while compression member has an opposing interior wall 348 generally facing interior wall 338. The interior walls 338 and 348 along with internal contact surface 313 define an access cavity 350 within the perianal support device. As shown in FIG. 16, the configuration of the base 310 as described above results in a generally wedge shaped device. Still further, with the inclusion of the access cavity 350, the base 310 has a substantially V-shaped configuration with the pressure surface 312 defined at the apex of the V and the compression members 330 and 340 forming the legs of the V.

Figure 17:
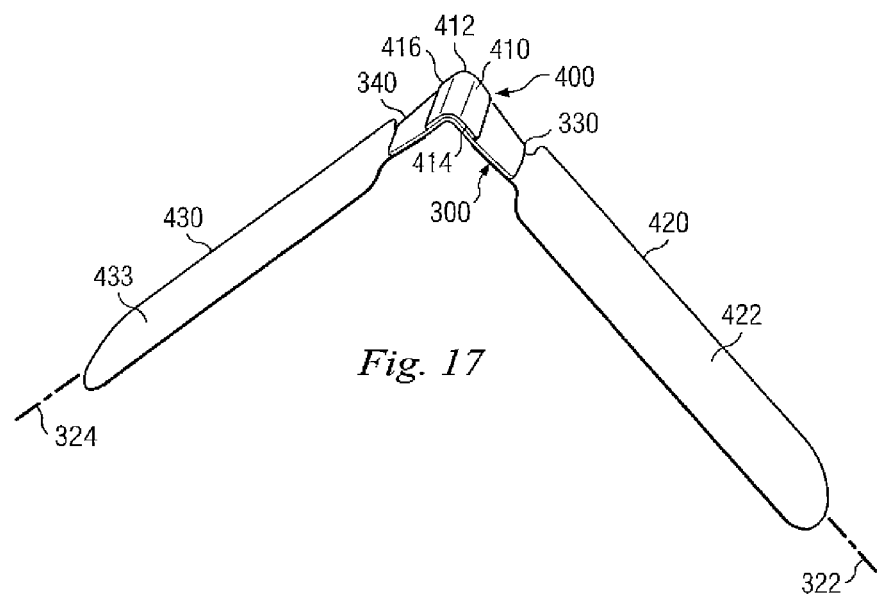
FIG. 17 is a perspective view of a system according to one aspect of the present invention.

Referring now to FIG. 17, there is shown an embodiment of a support system 400 according to another aspect of the present invention. Support system 400 includes perianal support device 300 as previously described with respect to FIGS. 14-16. A compliant pad 410 is adhered to the support device 300 across the majority of the pressure surface 312. As illustrated, a first portion 414 of the complaint pad 410 extends along and is adhered to distal portion 332 of compression member 330. In a similar manner, second portion 416 extends along and is adhered to distal portion 342 of compression member 340. In one embodiment, the compliant pad 410 is a sterile gauze pad. In another embodiment, the compliant pad 410 includes an internal cushioning structure, such as polyurethane, silicon, rubber, foam, cotton, etc, with a non-abrasive skin contact surface. In one embodiment, the compliant pad is die cut from 1776 and 1772 stock materials from 3M. Then bonding the resulting laminate on to the compression surface as the 1772 material has an adhesive back. In another embodiment, compliant pad 410 is an absorbent material adapted to absorb bodily fluids. It will be appreciated that the compliant pad 410 may make placement and maintenance of the support device 300 more comfortable for the patient. In addition, the surface of the pad 410 is configured to frictionally engage the patient's perianal tissue to inhibit movement between the support device 300, particularly the pressure surface 312 and the patient. In still a further aspect, compliant pad 410 includes a treating compound. The treating compound is disposed within the pad, applied on the surface, or a combination of both. Treating compounds useful for combination with pad 410 include, but without limitation to other compounds, antibacterial compounds, antibiotic compounds, sclerants, antimicrobial compounds, anti-inflammatory compounds, anti-fungal agents, anti-itching agents, humicants, moisture absorbing agents, gas absorbing agents, buffering agents for pH control, drying agents and the like and coagulants. In yet a further embodiment, pad 410 is not fixed to device 300 but is instead positioned on the patient in advance of positioning device 300 or is loosely held to device 300 has it is applied to the body. In this embodiment, device 300 maintains the position of the pad 410 relative to the patient's body and in particular the anal orifice.

The support system 400 also includes a mechanism for securing the position of the perianal support device 300. An elongated fixation member 420 is joined to internal surface 338 of compression member 330. At least a portion of surface 422 of fixation member 420 has an adhesive coating adapted for joining to a fixed object. In a similar manner, elongated fixation member 430 is fixed to the internal surface 348 of compression member 340. Likewise, surface 433 includes an adhesive coating that can fix the elongated member to another object. In one embodiment, the adhesive coating is adapted for releasably adhering to a patient's skin. In another embodiment, the adhesive is adapted for joining to an inanimate object or to itself. In this manner, the fixation members 420 and 430 can fix the position of the support device 300 relative to the operating table or other fixture near the patient. In the illustrated embodiment, the elongated fixation members 420 and 430 are formed of flexible tape. Further, while they have been described separately, in one embodiment, the elongated fixation members are formed by a continuous piece of material joined in the middle to the perianal support device 300.

Figure 18:
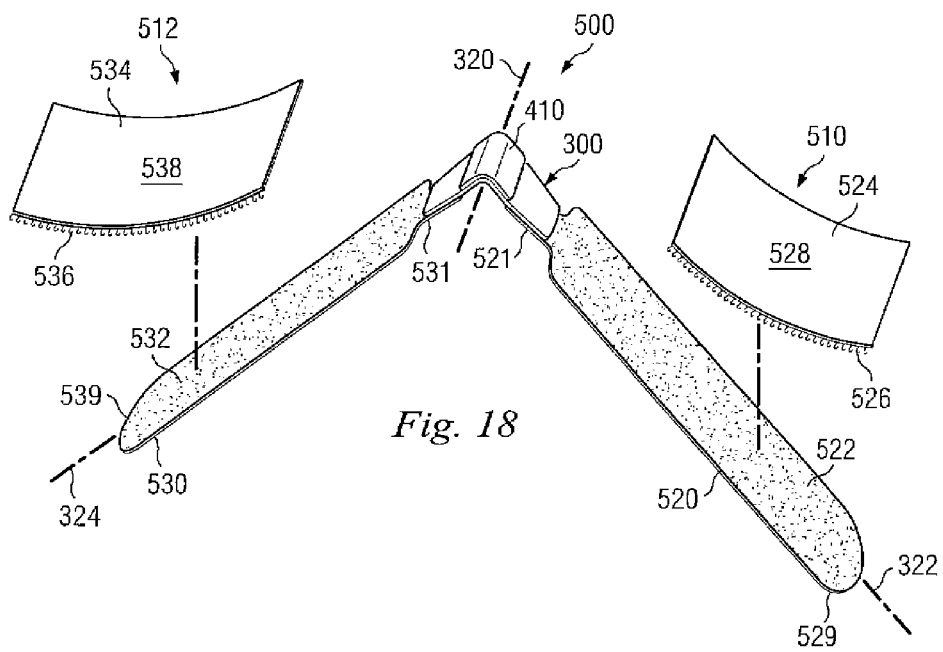
FIG. 18 is a perspective view of a further embodiment according to another aspect of the present invention.
Figure 19:
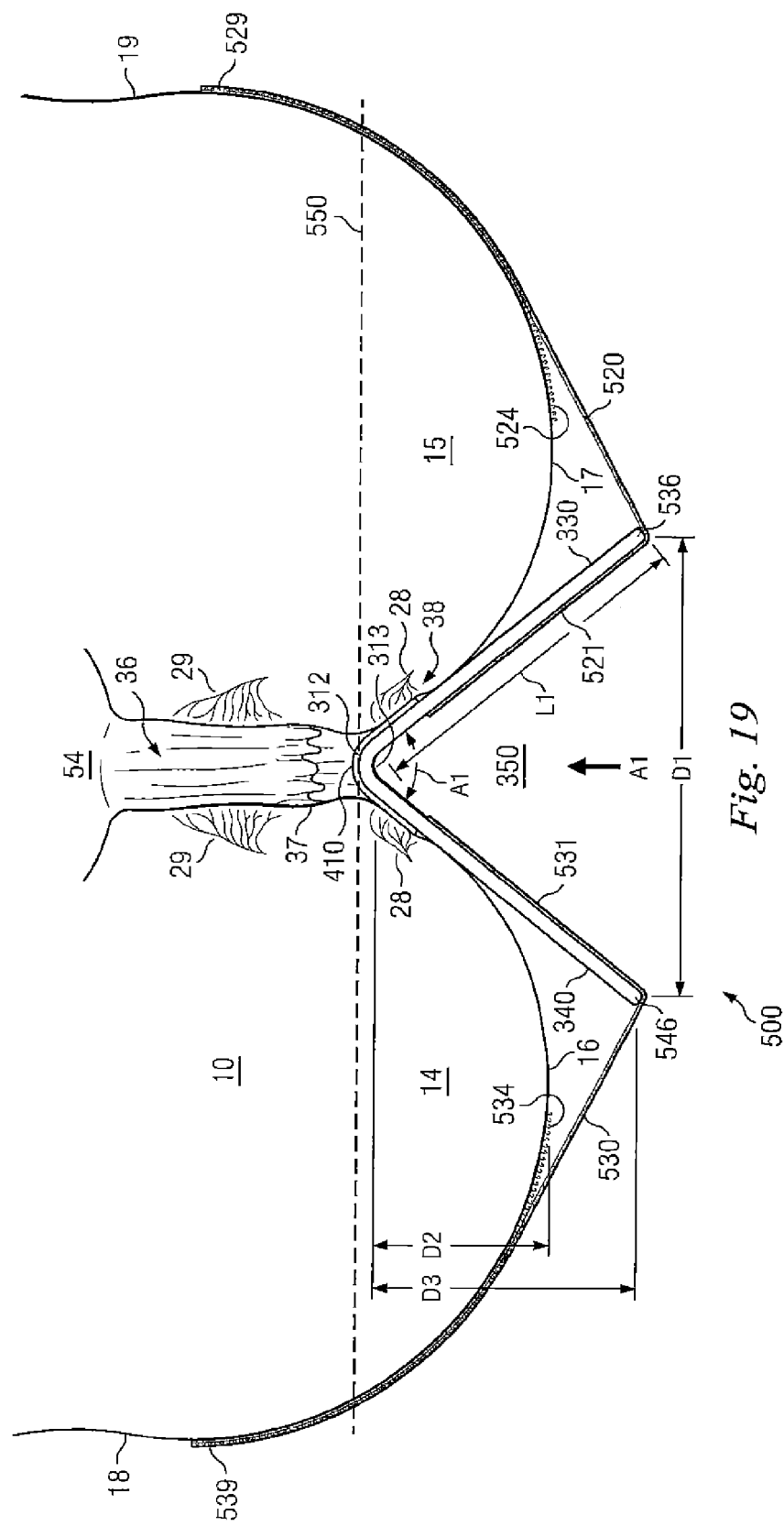
FIG. 19 is a partial cross sectional top view of the embodiment of FIG. 18 applied to a patient with stylized depiction of the patient anatomy.

Referring now to FIGS. 18 and 19, there is shown a support system 500 adapted to provide perianal support to a human patient. Support system 500 includes the perianal support member 300 and compliant pad 400 as discussed above. Complaint pad 410 is oriented to extend along the midline axis 320 to thereby form a contact surface oriented along the midline axis. In the illustrated embodiment, the midline axis also corresponds to the apex of the V-shaped support member. As an alternative to the embodiment illustrated in FIG. 17, the support system of FIG. 18 includes a pair of two part securing mechanisms. The first securing mechanism 510 includes an elongated fixation member 520 joined to the support device 300 at medial end 521 and extending generally laterally away from midline axis 320 in the direction of axis 322 toward lateral end 529. The fixation member includes a first half of a releasable fastening system on surface 522, such as a hook and loop system or a releasable adhesive system. The second component of the securing mechanism 510 includes an anchor pad 524. In the illustrated embodiment, anchor pad 524 has a generally square shape that is shorter in length and wider than elongated fixation member 520. The shape of the anchor pad is shown for illustration purposes and may take any form that is suitable for fixing to a patient or inanimate object, as well as joining to the elongated fixation member. Anchor pad 524 includes a first surface 528 having an adhesive surface adapted for joining to the patient's skin or some inanimate object. The opposing surface 526 includes the second half of the releasable fastening system. In a similar manner, the second securing mechanism 512 includes an elongated fixation member 530 joined to the support device 300 at medial end 531 and extending generally laterally away from midline axis 320 in the direction of axis 324 toward lateral end 539. The fixation member includes a first half of a releasable fastening system on surface 532, such as a hook and loop system or a releasable adhesive system. The second component of the securing mechanism 512 includes an anchor pad 534. In the illustrated embodiment, anchor pad 534 has a generally rectangular shape that is shorter in length and wider than elongated fixation member 530. Anchor pad 534 includes a first surface 538 having an adhesive surface adapted for joining to the patient's skin or some inanimate object. The opposing surface 536 includes the second half of the releasable fastening system.

As shown more clearly in FIG. 19, each compression member 330/340 has a length L1 and extends away from each other by an angle A1. The maximum lateral distance of the access cavity is defined by the distance D1 extending between distal ends 536 and 546. In one embodiment, L1 is greater than 4 cm in length. In a preferred aspect, L1 is approximately 8 cm. In one embodiment angle A1, is between 140 degrees and 30 degrees. In the illustrated embodiment, angle A1 is approximately 80 degrees. In one embodiment, the maximum lateral distance D1 of the access cavity is greater than 4 cm. In the illustrated embodiment of FIG. 19, the maximum lateral distance is approximately 10 cm. It will be understood that while compressive members 330/340 are sufficiently rigid to transmit compressive force toward the pressure surface, in one embodiment they are flexible, at least laterally, to bow or bend in response to force applied to the fixation members 520/530. In contrast, the anterior to posterior distance of the pressure surface 312 between first end 314 and second end 316 is approximately 5 cm in the illustrated embodiment (FIG. 14). This midline length between the first end 314 and the second end 316 of the device 300 can be adjusted in some embodiments depending on the amount and extent of perianal tissue that needs to be supported.

Figure 20:
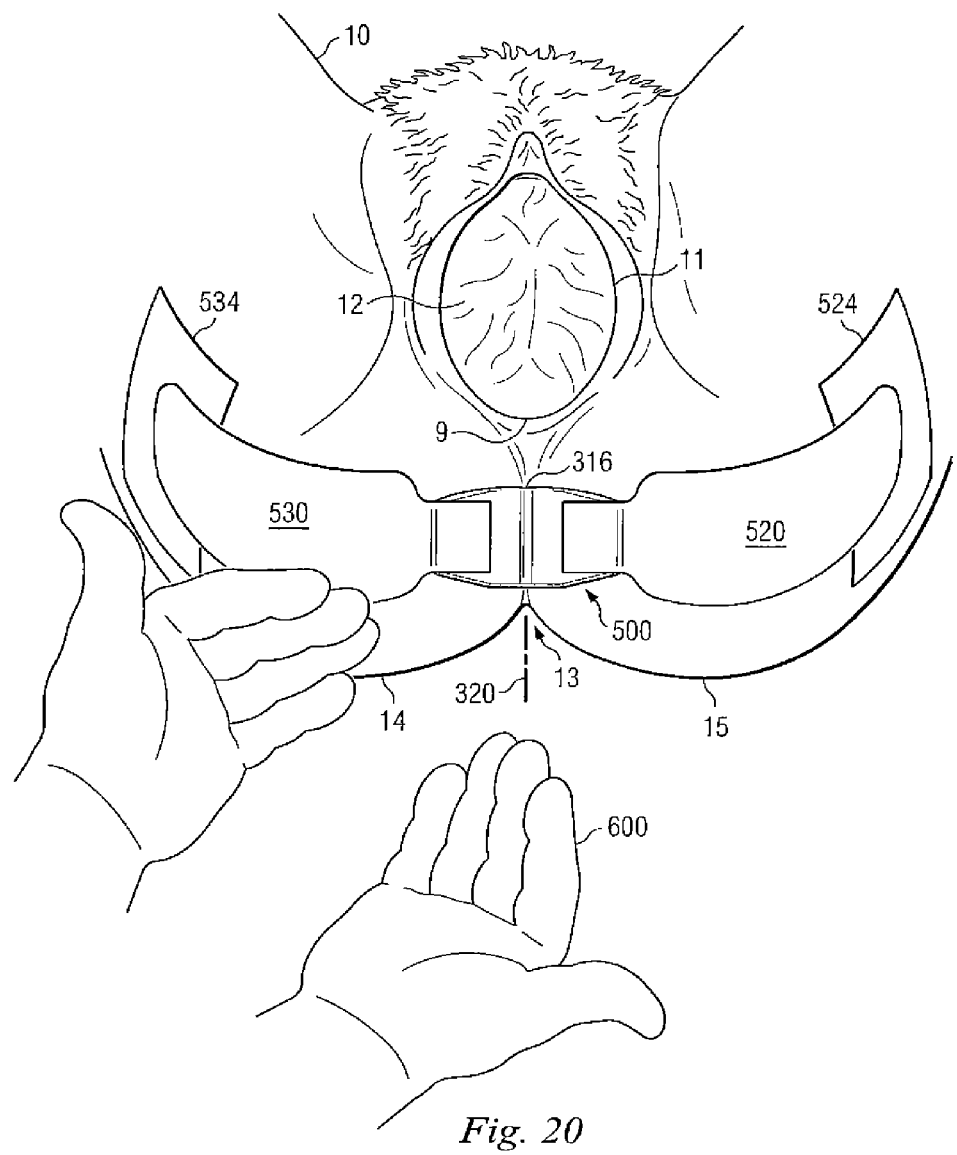
FIG. 20 is a partial perspective view of a device according to the present invention applied to a patient during child delivery.

Referring now to FIGS. 19 and 20, the support system 500 is illustrated in association with the perianal tissue of a patient 10. The patient 10 is shown in partial cross section to illustrate a portion of the rectum 54, anal canal 36, anal orifice 38, internal venous plexus 29, pectinate line 37 (also known as the dentate line), and external venous plexus 28. The patient's buttocks 14 and 15 are shown with the crown of the buttocks 16 and 17, respectively, laterally adjacent the perianal region. The buttocks 14 and 15 extend laterally beyond crowns 16 and 17 toward lateral flanks 18 and 19, respectively. The depth in the saggital plane of the gluteal cleft 13 from the anal orifice 38 to the buttocks crown 16 is shown by distance D2. The lateral flanks 18 and 19 may include, for example but without limitation, all or a portion of the buttocks, hips, or upper thigh of the patient.

In use, a health care provider positions the patient to expose the perianal region. In the child birthing process, the patient may be positioned in stirrups attached to a delivery table. Anchor pads 534 and 524 are adhered to the patient's skin on the lateral flanks 18 and 19, respectively. As best seen in FIG. 20, the anchor pads 524 and 534 are positioned on the lateral flanks 18 and 19 laterally adjacent the junction of the femur with the pelvis. The perianal support device 300 is then moved adjacent the gluteal cleft 13 between buttocks 14 and 15. The midline 320 of the support device is generally aligned with the patient midline within the sagittal plane. The support device is advanced in the direction of arrow A1 toward the anal orifice 38 (generally within the sagittal plane) to bring pad 410 into contact with the perianal tissues. Continued advancement of the support device toward the anal canal applies pressure through the pressure surface 312 and pad 410 to the perianal tissues. In one aspect, the healthcare provider places at least one finger within the access cavity 350 and preferably against internal contact surface 313 to advance the device against the anal orifice. In another aspect, an instrument having complimentary engagement surface to at least a portion of the access cavity 350 is used to apply pressure to the device 300. With continued pressure applied by the healthcare provider to the access cavity 350, and/or internal contact surface 313, elongated fixation member 520 is extended laterally of the anal orifice 38 out of the gluteal cleft 13 and releasably attached to anchor pad 524 with at least lateral end 529 extending adjacent lateral flank 19. In a similar manner, with compressive force still applied by the healthcare provider to support device 300, elongate fixation member 530 is extended laterally of the anal orifice 38 out of the gluteal cleft 13 and is secured to anchor pad 534 with at least lateral end 539 extending adjacent lateral flank 18. Thus, the fixation members 520 and 530 of the system 500 do not extend along the gluteal cleft 13 with the potential for interference with the birthing process but instead extend substantially laterally from the patient's midline out of the gluteal cleft 13.

The extent of tissue deformation surrounding the anal orifice 38 is a function of the patient anatomy and of the amount of compressive force applied during application of the support device 300. In one aspect, the health care provider makes initial contact with anal orifice 38 and then applies pressure in the saggital plane (generally toward the patient's head) to advance the device 1 cm to 3 cm. This advancement of the device approximately 1 cm to 3 cm compresses the perianal tissue and thereby supports the tissue to inhibit distention as the patient pushes during the birthing process. It will be appreciated that with the illustrated embodiment, the healthcare provider may reposition the device and adjust the compressive force applied through the compression members 330 and 340 to the pressure surface 312 by releasing or adjusting the attachment between the anchor pads 524/534 and the fixation members 520 and 530

In an alternative approach, the pad 410 and pressure surface 312 are positioned in engagement with the anal orifice with little if any compressive force applied to deform the perianal tissue. The support device is then secured in position as described above. With this technique, the support device will resist movement of the device in a direction generally away from the patient's head and will thereby support the perianal tissue to maintain its position.

As shown in FIG. 19, the distance D2 between the anal orifice and the buttocks crown 16 is less than the distance D3 between the distal end 546 of compression member and the anal orifice. The distance D3 represents the length or extent of the compression member 340 as measured in the saggital plane. In one aspect, this length is greater than 3 cm. In another aspect, as shown, the distance D3 is approximately 6 cm. Thus, tension applied to fixation member 530 is transferred through compression member 340 to exert a compressive force on pressure surface 312. As previously described above with respect to FIG. 4, tension force applied to the flexible fixation members in the direction of arrows A2 and A3 are converted to compressive forces A4 and A5, respectively resulting in compression at the pressure surface 312 in the direction of arrow A1 directed inwardly toward the anal orifice.

Referring now to FIG. 20, with system 500 in position, a healthcare provider is allowed to position one or both hands 600 within the access cavity 350 extending into the gluteal cleft. In this manner, the hands 600 may be below the lowest portion 9 of the vaginal opening 11 as the head of the baby 12 passes out of the vagina. Thus, the hand within the access cavity 350 is positionable less than 1 cm from the mother's vaginal opening or perineum so the healthcare provider may support the head of the baby as is it is being born. The position of second end 316 of the support device 300 also allows access to the tissue immediately below the vaginal opening 11 in the event an obstetric maneuver, such as an episiotomy, manipulation of the fetus, etc., is necessary. Further, as discussed above, in one aspect the support device 300 is quickly repositioned or removed by releasing at least one of the straps from the anchor pads, an obstetric maneuver is performed, the device 300 is repositioned in a supporting position adjacent the anus and the anchoring straps are repositioned on the anchor pads.

In one embodiment, the support system is formed of biocompatible material suitable for contact with human tissue. Moreover, in one embodiment, the device is provided sterile in a package for single use application on a patient, although reusable devices according to the present teachings are also disclosed in the present description. In the single use type of embodiment, the device is cost effectively manufactured such that it is discarded after use. For example, the device 300 is formed by of a substantially rigid polycarbonate material. In one aspect, the device 300 is injection molded to substantially its final V-shaped form. The compliant pad 412 is then applied to the apex and fixation members 520 and 530 are joined to the compression members via an adhesive. It is contemplated that fixation members 520 and 530 may be riveted, snapped or otherwise fixedly attached to the compression members. Still further, in a different embodiment, fixation member 520 is passed through a channel or other opening associated with the compression members to loosely and/or removably join the fixation member to the compression device. In one aspect, compression member 520 is a loop portion of a hook and loop fastening system, such as sold under the tradename VELCRO.

It is contemplated that in other embodiments, the device 300 is formed by compression molding, transfer molding, reactive injection molding, extrusion, blow molding, casting, heat-forming, machining, deforming a sheet, bonding, joining or combinations thereof. In other embodiments, suitable materials for device 300 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polyproplylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc.

It is contemplated that in still further embodiments, the complaint pad 412 can be made from or includes at least one of the following, either alone or in combination: woven fabric, non-woven mesh, foam, film, porous sheet, and non-porous sheet. At least the device 300 and compliant pad 412 are sterilized by know techniques; such as ethylene oxide gas, gas plasma, electron-beam radiation or gamma radiation. Such materials are available from various suppliers such as 3M. In a similar manner, the fixation members or straps may be formed of hook and loop fastening systems available from 3M. Adhesive fixation systems may be adhesive a Rayon woven tape on a liner (1538L from 3M). The tape may include liners to prevent premature tape adhesion. In one embodiment, the liners include a cut between the midline end adjacent device 300 and the lateral end. During initial placement, the device is pushed against the anus with a first hand. The opposite hand spreads the butt check away from the device while the first hand pushes the base to get further compressive penetration in the gluteal cleft. The hands are switch and the steps are repeated on the opposite butt check. After position the device, the liners adjacent the device 300 are sequentially removed and adhered to the medial portion of the buttocks for provisional positioning of the device. Once the device is provisionally positioned, the first lateral liner is removed and with pressure applied to the device, the lateral tape segment is adhered to the patient in a final supporting position to supply compressive force to the device. This step is repeated on the opposite side for final fixation.

The present invention also contemplates a kit that includes one or more of the components described above provided in a package. In one embodiment, the kit includes at least a sterilized perianal support device. In another aspect, the kit further includes an anchoring assembly as described above. In this embodiment, the anchoring assembly may be preassembled with the perianal support device as shown in the drawings or may be provided unassembled. In the unassembled kit, a health care provider will remove the support device and anchoring assembly from the packaging and assembly the support device with the anchoring assembly. As set forth above, the anchoring assembly may be adhered to the support assembly near the patient or the support assembly may include fastening, members or apertures to receive elements of the anchoring assembly. For example, the support device may include an aperture and a portion of a flexible strap may be threaded through the aperture to join the two components. In still a further embodiment, the kit includes a treating compound to apply to the patient. In one such embodiment, the treating compound is provided in a separate package. In an alternative embodiment, the treating compound is applied to or incorporated into the support device on the perianal contact surface.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment.

What is claimed is:

1. A kit for providing perianal support, the kit comprising:
a perianal support a pressure surface
dimensioned and configured to engage at least a portion of
the perianal tissue on opposing sides of the anal orifice of a patient, and a compression member operatively joined to said compression body and extending therefrom, said compression member being sized to extend beyond the buttocks crown of the patient when the compression body is engaging said at least a portion of the perianal tissue; and a compression system configured to apply loading on the compression member at a location beyond the buttocks crown of the patient in a manner causing the compression surface to engage and apply compressive loading to said at least a portion of the perianal tissue.

2. The kit of claim 1, wherein the compression system includes at least one strap pre-assembled with the support body.

3. The kit of claim 1, wherein the compression system is provided in the kit separate from the support body.

4. The kit of claim 1, further including a treating compound.

5. The kit of claim 4, wherein the treating compound is provided in a separate package within the kit.

6. The kit of claim 4, wherein the treating compound is provided on the support body within the kit.

7. A kit for providing perianal support, the kit comprising:
a support body having a perianal tissue pressure member extending along a midline axis, the pressure member dimensioned and configured to span across an anal orifice, to engage perianal tissue of the patient adjacent the external venous plexus on opposing sides of the anal orifice and to not extend into the anal orifice beyond the pectinate line, the support body including a compression member having a proximal portion, a distal portion, and a longitudinally extending axis substantially transverse to the midline axis, the compression member defining a compression member plane; and a lateral anchoring assembly configured to extend away from said body in a direction substantially transverse to the midline axis, wherein the lateral anchoring assembly comprises a flexible fixation member extending from the support body, the fixation member being arranged to extend along the longitudinal axis of the compression members when the flexible fixation member is disposed in the respective plane defined by the compression member.

8. The kit of claim 7, wherein the lateral anchoring assembly is pre-assembled with the support body within the kit.

9. The kit of claim 7, further including a treating compound.

10. The kit of claim 9, wherein the treating compound is provided in a separate package within the kit.

* * * * *